(12) United States Patent
Pitts

(10) Patent No.: US 8,361,451 B2
(45) Date of Patent: Jan. 29, 2013

(54) MULTI-FUNCTIONAL, ALL-USE, ENVIRONMENTALLY-FRIENDLY (GREEN) SOAP

(76) Inventor: Thomas Pitts, New York, NY (US)

(*) Notice: Subject to any disclaimer, the term of this patent is extended or adjusted under 35 U.S.C. 154(b) by 356 days.

(21) Appl. No.: 12/636,692

(22) Filed: Dec. 11, 2009

(65) Prior Publication Data

US 2011/0142782 A1   Jun. 16, 2011

(51) Int. Cl.
*A61L 9/01* (2006.01)
*A61K 8/02* (2006.01)

(52) U.S. Cl. ....... 424/76.1; 510/140; 510/142; 510/143; 424/76.4

(58) Field of Classification Search ............. 424/76.1; 510/140
See application file for complete search history.

(56) References Cited

U.S. PATENT DOCUMENTS

| | | | | |
|---|---|---|---|---|
| 4,081,394 A | * | 3/1978 | Bartley | 510/146 |
| 4,438,010 A | * | 3/1984 | Lindauer et al. | 510/143 |
| 5,221,506 A | * | 6/1993 | Dulin | 510/120 |
| 2007/0172303 A1 | * | 7/2007 | Ho | 401/143 |

* cited by examiner

*Primary Examiner* — Frederick Krass
*Assistant Examiner* — Adam C Milligan

(57) ABSTRACT

A bar of soap that will help the environment, solve an age old problem of what to do with the annoying pieces of leftover soap, save consumers money by using the complete bar of soap and provide additional functions from one bar of soap.

5 Claims, 9 Drawing Sheets

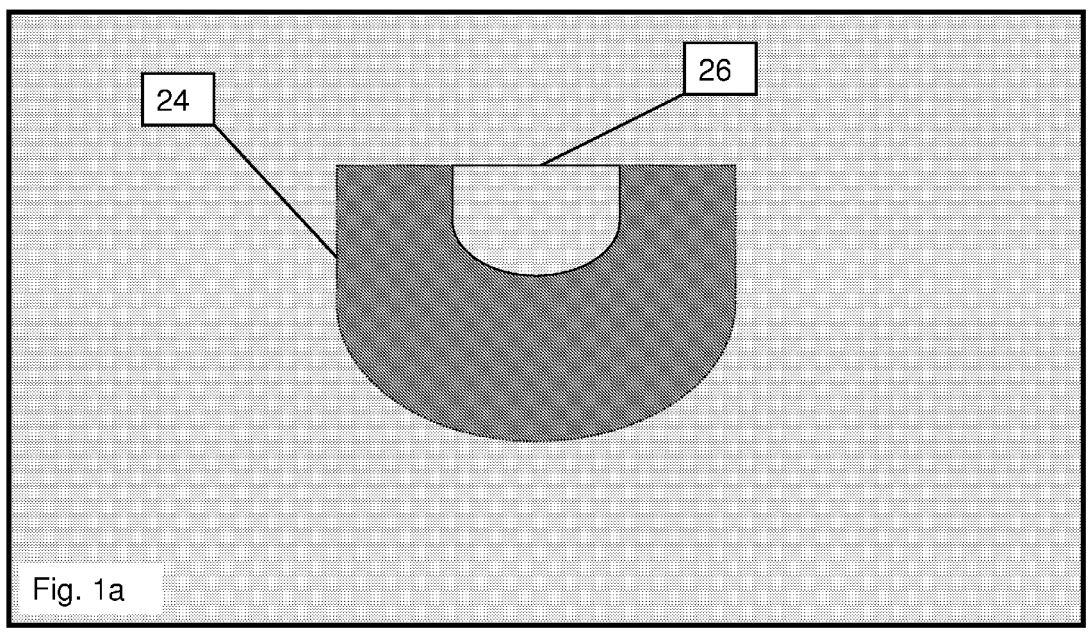

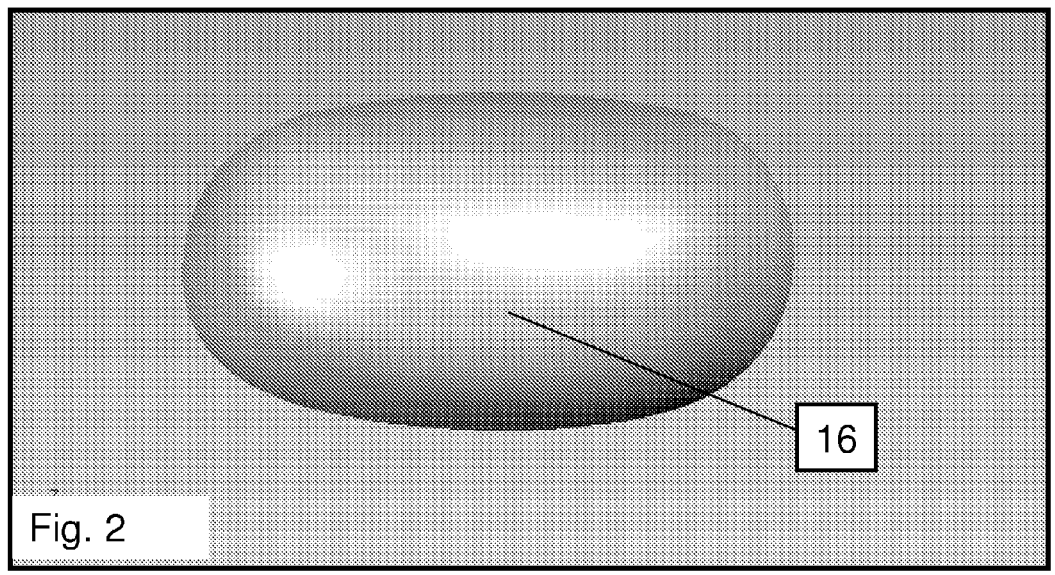
Outer soap portion side view

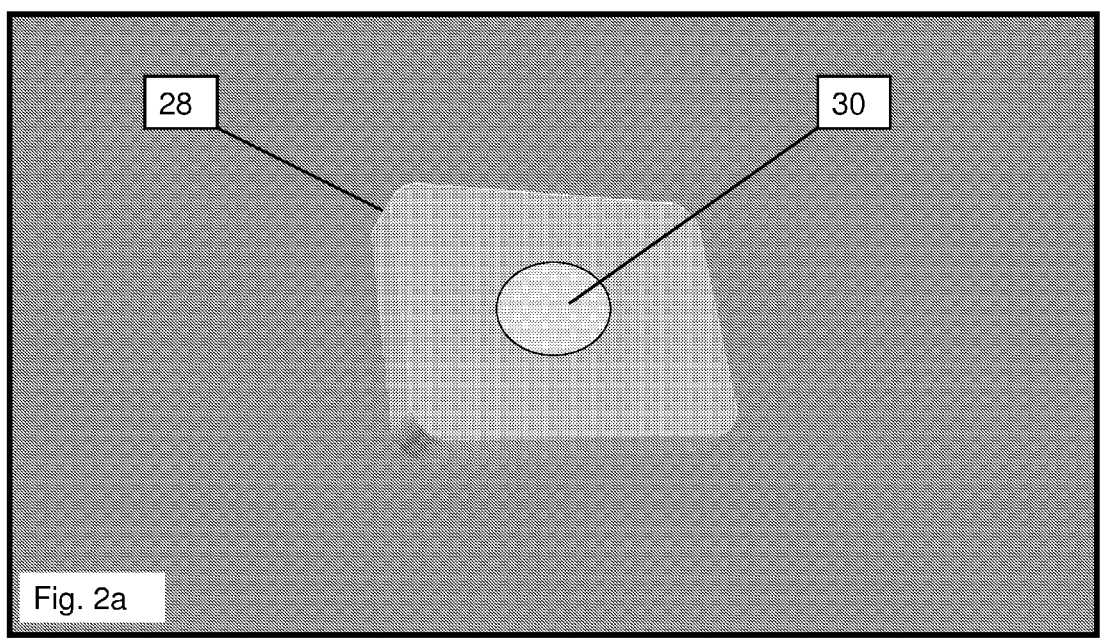

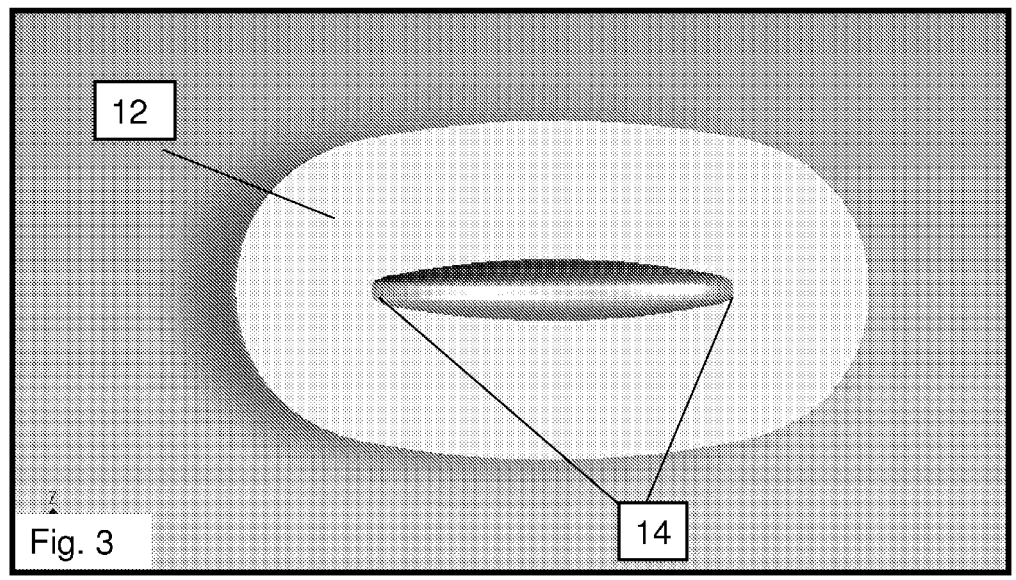
Center view of outer soap portion with inner portion inlay section.

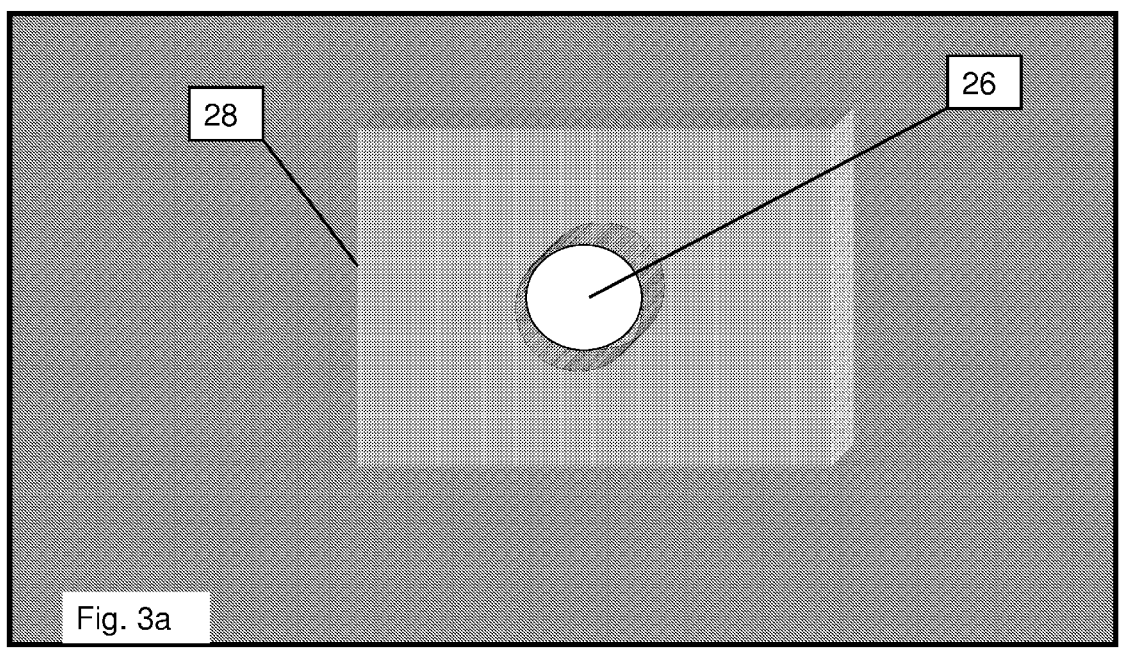

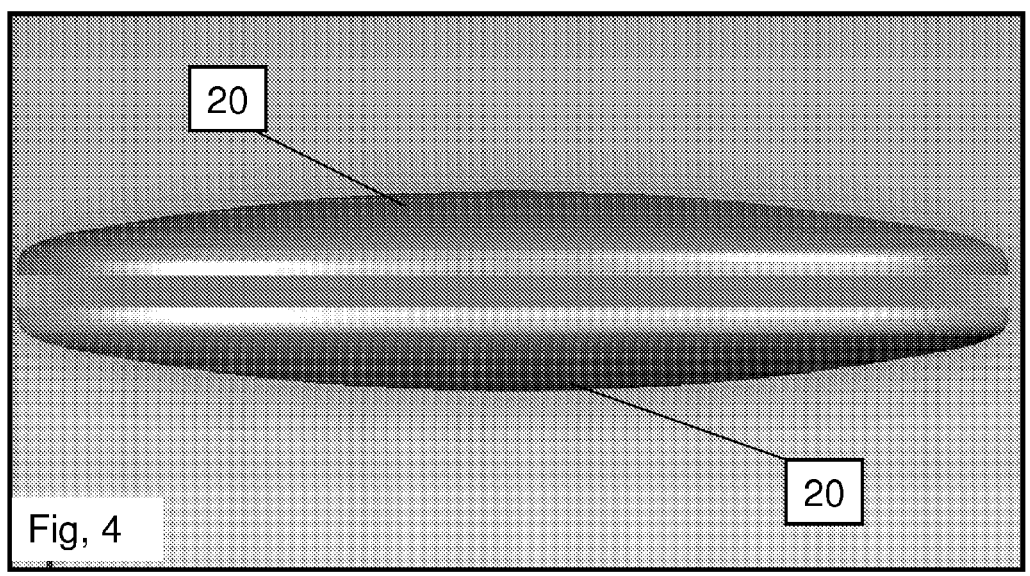
Inner soap portion dissected view.

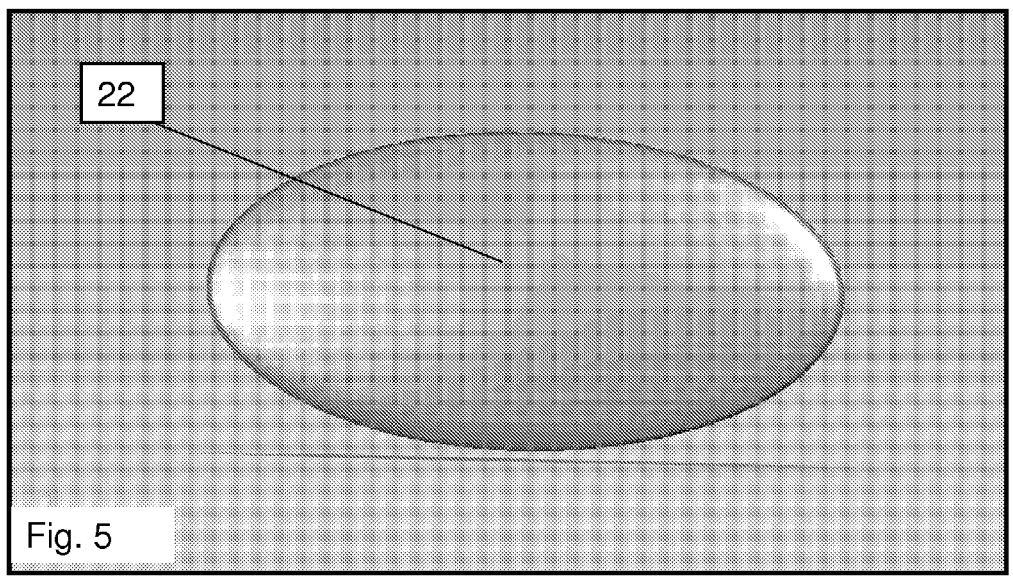
Inner soap portion side view

MULTI-FUNCTIONAL, ALL-USE, ENVIRONMENTALLY-FRIENDLY (GREEN) SOAP

CROSS-REFERENCE TO RELATED APPLICATIONS

Not Applicable

STATEMENT REGARDING FEDERALLY SPONSORED RESEARCH OR DEVELOPMENT

Not applicable

REFERENCE TO SEQUENCE LISTING, A TABLE, OR A COMPUTER PROGRAM LISTING COMPACT DISK APPENDIX

Not Applicable

BACKGROUND OF THE INVENTION

The present invention is in the technical field of personal care. More particularly, the present invention is in the technical field of full function and multifunction soap products.

BRIEF SUMMARY OF THE INVENTION

The present invention is an environmentally-friend soap that carries several functions; cleans body parts, deodorizes several areas of the home, moisturizes the skin, provides a scented lucky charm and can be used as a candle.

BRIEF DESCRIPTION OF THE SEVERAL VIEWS OF THE DRAWING

There are two styles presented.

FIG. 1a is the same (as FIG. 1) perspective view of a dissected soap outer portion of present invention in a different version (shape and form)

FIG. 2 is a side view of an outer soap portion of the present invention; FIG. 2a is the same (as FIG. 2) side view of an outer soap portion of the present invention in a different version (shape and form)

FIG. 3 is a center view of a outer soap portion with inner portion inlay section of the present invention; FIG. 3a is the same view (as FIG. 3) view of a outer soap portion with inner portion inlay section of the present invention;

FIG. 4 is a perspective view of a dissected soap inner portion of the present invention; and FIG. 5 is side view of a inner soap portion of the present invention.

DETAILED DESCRIPTION OF INVENTION

Figure 1:
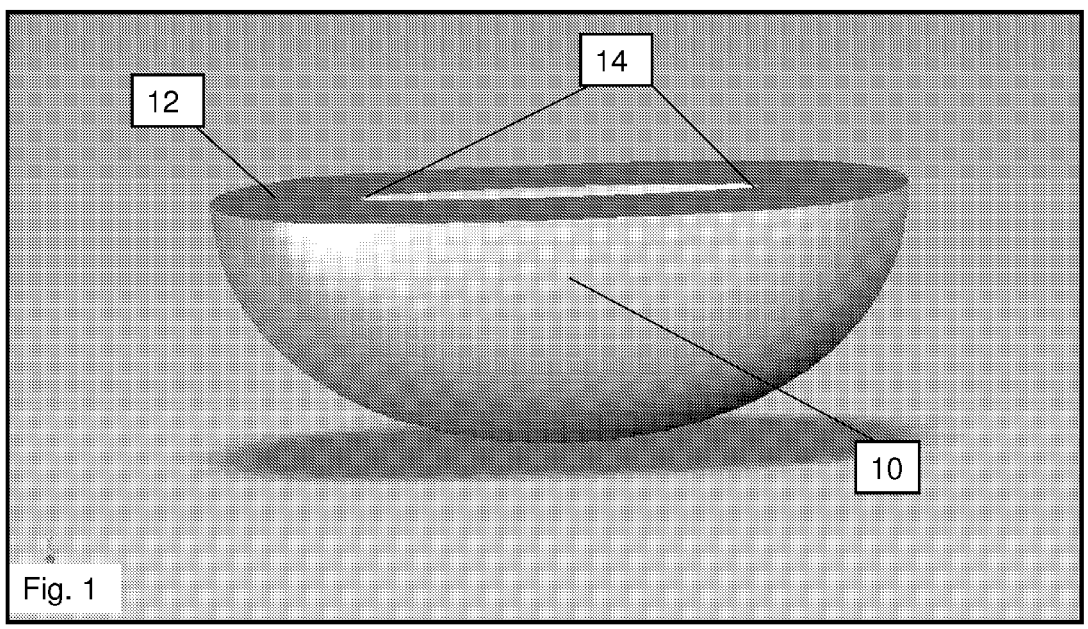
FIG. 1 is a perspective view of a dissected soap outer portion of the present invention.

Referring now to the invention in more detail, in FIG. 1 to 5a there is shown

| Item # | Description |
|---|---|
| 10, 24 | Side view of the bar of soap dissected |
| 14, 26 | Opening where center insert will be placed |
| 16, 28 | Complete side view of the bar of soap |
| 20, 22, 30 | Center inserts for the bar of soap |

In more detail, still referring to the invention of FIG. 1 to 5a. The bar of soap in FIG. 2, complete bar 16 and FIG. 2a, complete bar 28 and 30 combined, will be used as a organic, environmentally-friendly (green) soap, that has health benefits. Once the soap is used down to the inner core FIG. 1, core 14 and FIG. 2a, core 30 the soap can and will be used for other purposes, i.e. air freshener, hand moisturizer, scented good luck charm or candle. Center core pieces FIG. 5, core 22 and FIG. 5a, core 30 will be of an organic matter that is scented and made of a hand moisturizer and wax composition.

Figure 5A:
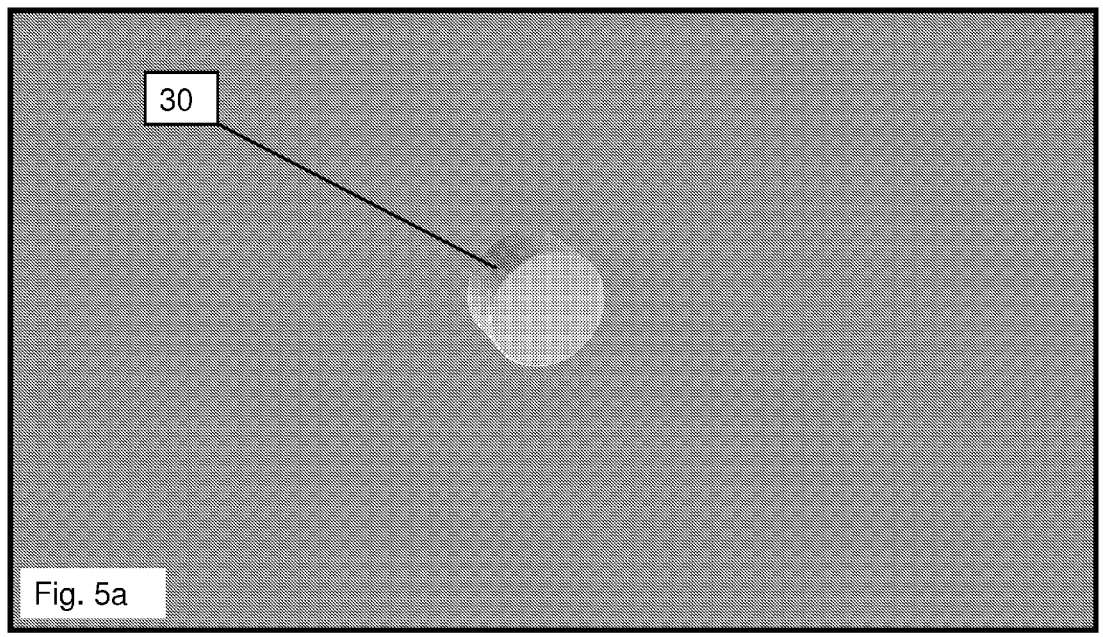
FIG. 5a is the same (as FIG. 5) is side view of an inner soap portion of the present invention.

In further detail, still referring to the invention of FIG. 1 the outer bar of soap 10, is approximately 4 inches long, 1¾ inches thick and 2¾ inches wide. Along with FIG. 2a the complete bar of soap 28 and 30 combined are approximately 4 inches long, 1¾ inches thick and 2¾ inches wide. In FIG. 5 the inner section core 22, is approximately 1½ inches long, ½ inch thick and 1 inch wide. Along with FIG. 5a the inner core 30, is approximately 1¾ inches thick with a 1 inch diameter. The construction details of the invention as shown in FIG. 5 made of a organic, environmentally friendly (green) health conscious material that can be used for air-fresheners, skin moisturizers, candles 22, that is approximately 1½ inches long, ½ inch thick and 1 inch wide will be inserted to FIG. 1 made of organic, environmentally-friendly (green) soap material 10 into space 14 that is approximately 1½ inches long, ½ inch thick and 1 inch wide. Alike FIG. 5a made of a organic, environmentally friendly (green) health conscious material that can be used for air-fresheners, skin moisturizers, candles 30, that is approximately 1¾ inches thick with a 1 inch diameter will be inserted to FIG. 3a made of organic environmentally-friendly (green) soap into space 26, that is approximately 1¾ inches thick with a 1 inch diameter.

Referring now to the invention shown in FIG. 1 versus FIG. 2a which show the two different designs but sharing the same exact functionalities of the invention.

The advantages of the present invention include, with out limitation, an organic, environmentally friendly, green soap that has several functions and also solves the age old problem of what to do with the wasted annoying pieces of soap, that are never used. This invention has several secondary usages such as air fresheners, skin moisturizers, scented good luck charm and candle. This invention will also save money and time by utilizing the product to its full potential and assist with the environmental health.

In broad embodiment, the present invention is a bar of soap that will help the environment, solve an age old problem of what to do with the annoying pieces of leftover soap, save consumers money by using the complete bar of soap and provide additional functions from one bar of soap.

While the foregoing written description of the invention enables one of ordinary skill to make and use what is considered presently to be the best mode thereof, those of ordinary skill will understand and appreciate the existence of variations, combinations, and equivalents of specific embodiment, method, and examples herein. The invention should therefore not be limited by the above described embodiment, method, and example, but by all embodiments methods within the scope and spirit of the invention as claimed.

I claim:

1. A soap bar comprising:
   an outer soap portion, wherein the outer portion comprises soap and measures approximately 4 inches long, 1.75 inches thick and 2.75 inches wide, and
   an inner portion, wherein the inner portion is a natural wax candle and measures approximately 1.75 inches thick with a 1 inch diameter.

2. The soap bar of claim 1, wherein the outer portion is made of all natural ingredients.

3. The soap bar of claim 1, further comprising packaging.

4. The soap bar of claim 3, wherein the packaging is made of all natural products.

5. The soap bar of claim 3, wherein the packaging comprises:
 a storage and carrying pouch for the soap bar, and
 a washcloth and exfoliating tool.

* * * * *